United States Patent [19]
Gross et al.

[11] Patent Number: 5,149,654
[45] Date of Patent: Sep. 22, 1992

[54] INCUBATION DEVICE FOR MICROTITER PLATES

[75] Inventors: Jürgen Gross, Hofheim am Taunus; Holger Pufahl, Frankfurt am Main; Dieter Sänger, Niedernhausen; Karl-Heinz Schaller, Schöneck; Hugo Wilmes, Eschborn, all of Fed. Rep. of Germany

[73] Assignee: Hoechst Aktiengesellschaft, Marburg, Fed. Rep. of Germany

[21] Appl. No.: 603,953

[22] Filed: Oct. 26, 1990

[30] Foreign Application Priority Data

Nov. 21, 1989 [DE] Fed. Rep. of Germany ....... 3938565

[51] Int. Cl.$^5$ ............................ C12M 1/38; B65G 1/00
[52] U.S. Cl. ............................ 435/287; 435/809; 435/290; 236/3; 237/14; 237/3; 414/280; 414/282; 414/616
[58] Field of Search ............... 119/35, 37, 39, 40; 237/3, 14; 236/2, 3; 422/63; 435/809, 287; 436/809; 414/280, 282, 661

[56] References Cited

U.S. PATENT DOCUMENTS

| | | | |
|---|---|---|---|
| 447,453 | 3/1891 | Unland | 237/14 |
| 934,986 | 9/1909 | Adair | 237/14 |
| 3,883,008 | 5/1975 | Castaldi | 414/661 |
| 4,032,027 | 6/1977 | Lindberg | 214/16.6 |
| 4,356,967 | 11/1982 | Lunick | 237/14 |
| 4,572,427 | 2/1986 | Selfridge et al. | 236/3 |
| 4,689,303 | 8/1987 | Kraft et al. | 435/290 |
| 4,720,463 | 1/1988 | Farber et al. | 435/291 |
| 4,756,657 | 7/1988 | Kinney | 414/281 |
| 4,856,956 | 8/1989 | Zur | 414/280 |

*Primary Examiner*—Robert J. Warden
*Assistant Examiner*—Theresa A. Trembley
*Attorney, Agent, or Firm*—Finnegan, Henderson, Farabow, Garrett and Dunner

[57] ABSTRACT

An incubation apparatus for microtiter plates includes an heating chamber and a incubation chamber. The heating chamber has a controllable hot air generator over which are arranged air guide devices for equalizing and distributing a stream of hot air to the microtiter plates. Air return devices are provided for collecting and returning hot air to the hot air generator. The heating chamber can be closed by a gate, and incubation chamber is divided by shelves into a plurality of compartments for receiving the microtiter plates. It is possible to close each compartment with a gate, and the side walls of the compartments are provided with heating devices. Furthermore, the incubation apparatus is provided with a gripping and transporting device having a working platform that is vertically displaceable and having a horizontally displaceable gripping arm.

12 Claims, 4 Drawing Sheets

INCUBATION DEVICE FOR MICROTITER PLATES

BACKGROUND OF THE INVENTION

1. Field of the Invention

The invention relates incubation device for microtiter plates, which comprises a heating and incubation chamber.

2. Description of the Related Art

In immunological assays, such as, for example, enzyme-linked immunosorbent assays (ELISA), antigens which react with constituents of a patient's sample are immobilized on the surface of the vessel walls of a microtiter plate. The reactions take place with defined temperatures and incubation times.

SUMMARY OF THE INVENTION

An object of the present invention is to provide a device for the incubation of microtiter plates with whose aid the incubation process can take place automatically.

The invention achieves the object through an incubation device wherein a) the heating chamber has a controllable hot-air generator over which are arranged air-guide devices for the equalization and distribution of the stream of hot air to the microtiter plates, as well as air-guide devices for the collection and return of the hot air to the hot-air generator, the heating chamber being closable by a gate, b) the incubation chamber is divided into a plurality of compartments by shelves for receiving the microtiter plates, it being possible to close each compartment by a gate, and the side walls of the compartments being provided with heating devices, and c) the incubation device is provided with a gripping and transporting device whose working platform is vertically displaceable and which has a horizontally displaceable gripping arm.

The heating chamber and incubation chamber can form one module in which the gates for the individual compartments are arranged one above the other in a front section and are carried in lateral guides. The module can be provided with an arrangement for individual opening of the gates, which arrangement has a vertically and horizontally movable gripping arm for a catch which is arranged laterally on the gate. A storage hopper which has a feed device for the microtiter plates can be assigned to the module. The gripping and transporting device can be rotatable about its vertical axis.

The advantages of the incubation device may be regarded as essentially being that the heating of the microtiter plates is spatially separated from the actual incubation phase, which facilitates the maintenance of a constant temperature during the incubation phase. Furthermore, the incubation device can be integrated straightforwardly into automatically operating analytical equipment.

The invention is explained in detail hereinafter on the basis of drawings showing only one embodiment.

DESCRIPTION OF THE PREFERRED EMBODIMENT

Figure 1:
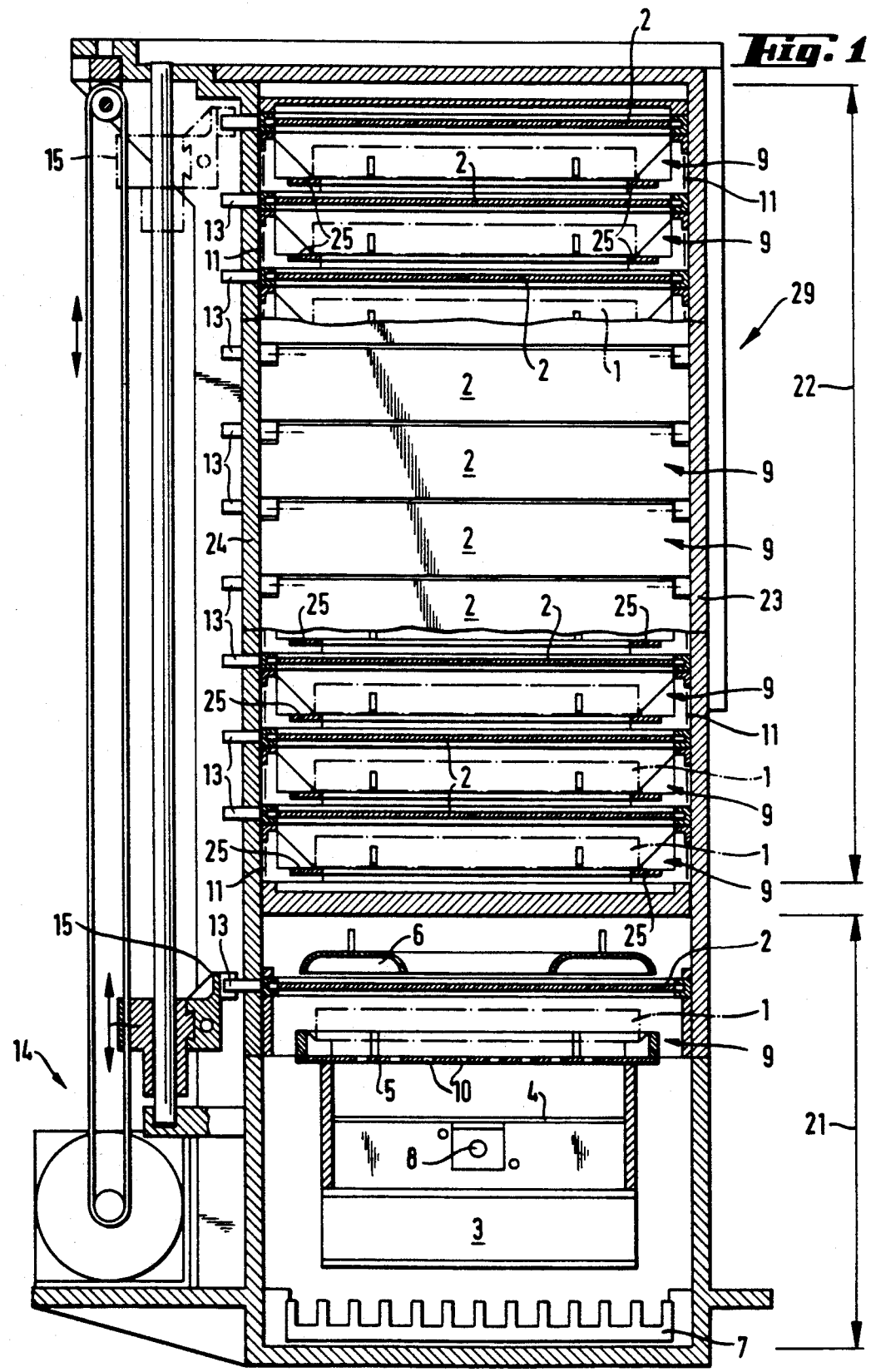
FIG. 1 is a partial cross-sectional view of module having a heating chamber and incubation chamber, in accordance with the present invention.

As shown in FIG. 1, the incubation device of the present invention includes a heating chamber (21) which is arranged spatially separated from an incubation chamber (22) together with the incubation chamber 22, module (29) for the incubation of microtiter plates.

A hot-air generator composed of a heating element (7) and aircirculation arrangement (3) is arranged in the heating chamber (21). Air-guide devices (4, 5), such as perforated plates (10), for the equalization and distribution of the stream of hot air to the microtiter plate (1) are located over the generator (3, 7). The used hot air is collected and returned to the heating element (7) via the air-guide devices (6). The heating chamber (21) can be closed by a gate and has a temperature sensor (8) which is part of a temperature control arrangement (not depicted). The heating time of the microtiter plate can be set as desired by suitable choice of the parameters required for the control.

Figure 2:
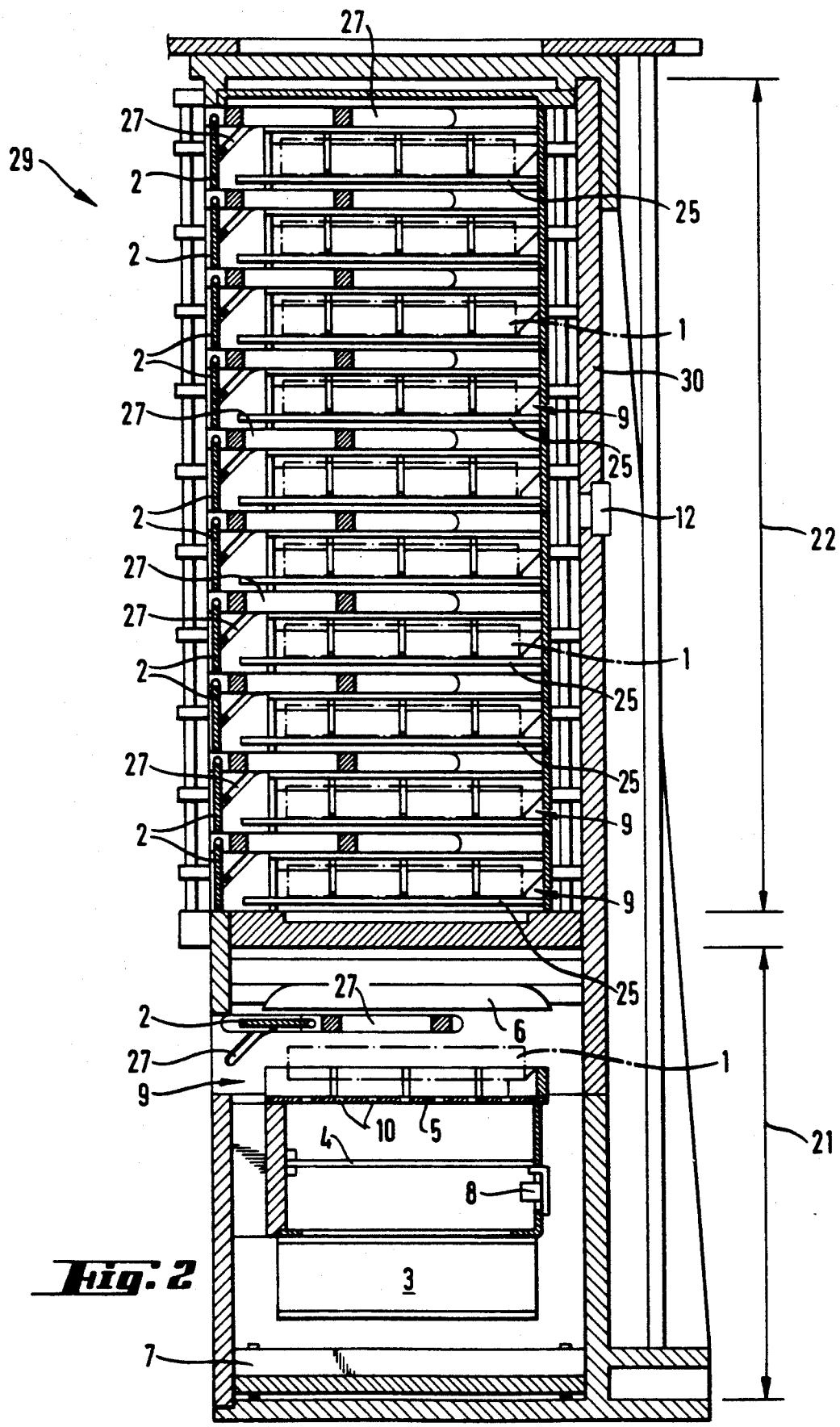
FIG. 2 is a cross-sectional lateral view of the module of FIG. 1.

The incubation chamber (22) is divided by shelves (25) into a plurality of compartments (9). The compartments (9) receive the microtiter plates (1) which are to be incubated. Each of them can be closed by a gate. Heating devices (11) are arranged on their lateral walls (23, 24). As shown in FIG. 2, a temperature sensor (12) is part of a control loop (not depicted) with whose aid the temperature in the incubation chamber (22) is kept constant.

The individual compartments (9) in the heating chamber (21) and in the incubation chamber (22) all have identical gates (2) and the same opening mechanism. The module (29) is provided with an arrangement (14) for the actuation of the gates (2), which has a gripping arm (15) arranged to be movable vertically and horizontally. The gates (2) are carried in lateral guides (27) which run partly at an angle and partly parallel to the shelves (25). The gates 2 have catches (13) by which they are drawn by the gripping arm (15) in the direction of the rear wall (30) for opening, and vice versa.

Figure 3:
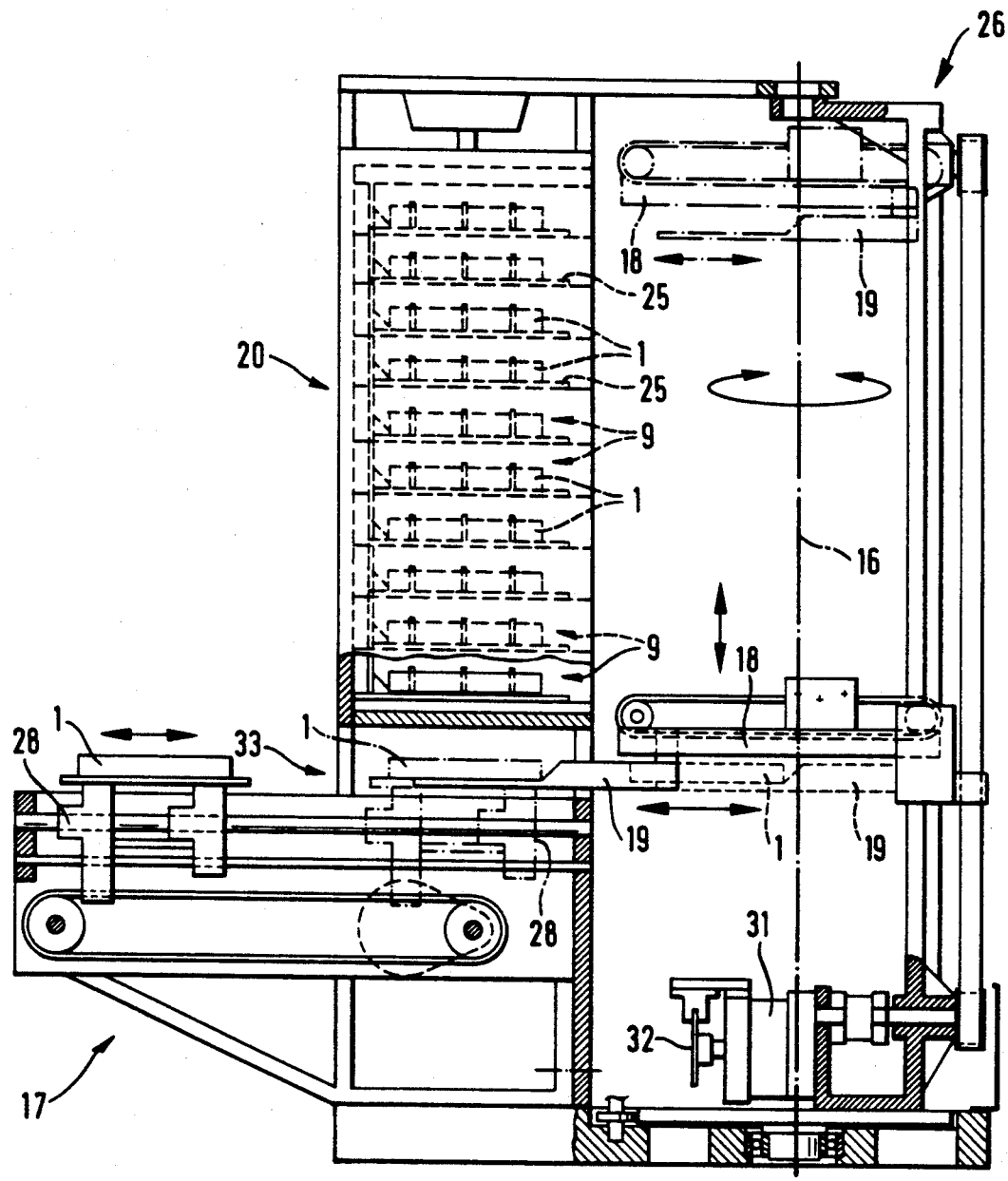
FIG. 3 is a cross-sectional lateral view of the storage hopper adjoined to the incubation device, in accordance with the present invention
Figure 4:
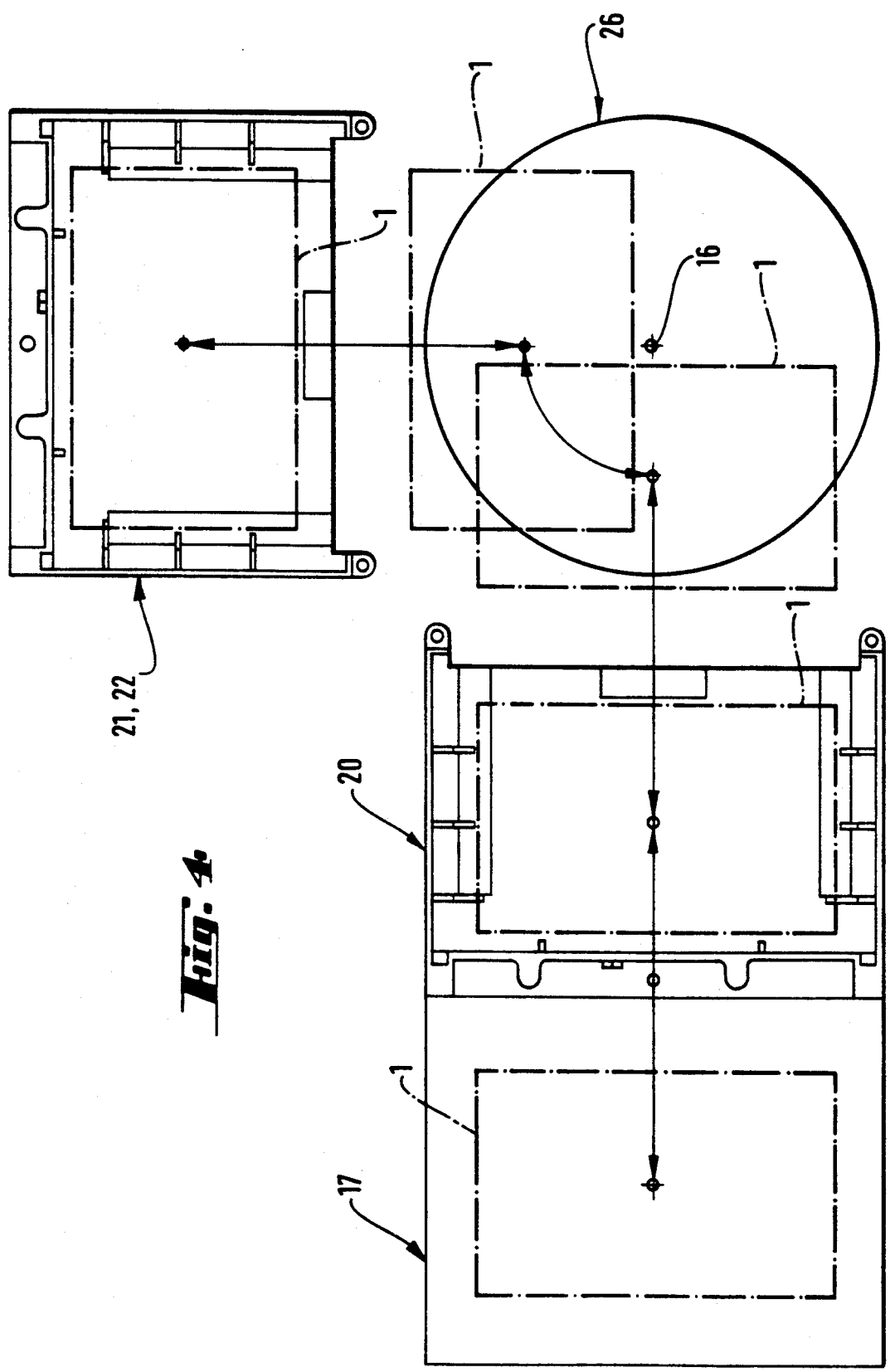
FIG. 4 shows a top view of the incubation device depicted in FIGS. 1-3.

As shown in FIG. 3, the incubation device is provided with a gripping and transporting arrangement (26) for loading and unloading the heating chamber (21) and the incubation chamber (22) with microtiter plates (1). A working platform (18) of transparting arrangement 26 is vertically displaceable and has a horizontally displaceable gripping arm (19). A drive motor (31) for moving the working platform (18) is provided with an identification disk (32) which is part of the motor control (not depicted). The drive for the gripping arm (19) can be equipped correspondingly.

Since the microtiter plates heated in the heating chamber (21) already have the desired final temperature, the thermal equilibrium in the incubation chamber (22) is not disturbed by loading with new microtiter plates.

A storage hopper (20) can be assigned to the module (29). The microtiter plates (1) which are to be incubated are stored therein. The hopper (20) expediently has just as many compartments as the incubation chamber (22). It also has a transfer station (33) which is provided with a feed device (17). The microtiter plates (1) are placed on the carriage (28) of the feed device (17) and conveyed into the transfer station (33). There the microtiter plates (1) are removed by the gripping and transporting device (26), which can be arranged to be rotatable about the axis (16), and placed in the compartments of the hopper (20). From there they pass into the heating chamber (21) and finally into the incubation chamber (22). It is also possible, by a suitable control device, to use the incubation device to carry out incubations which have to be interrupted by washing procedures and/or addition of reagents.

What is claimed is:

1. An incubation apparatus for microtiter plates, comprising:
   a heating chamber for holding a microtiter plate and including a controllable hot air generator, a gate for closing the heating chamber off from the outside environment, air guide means for equalizing and distributing a stream of hot air to a microtiter plate disposed in the heating chamber, and return means for collecting and returning hot air form the microtiter plate to the hot air generator;
   an incubation chamber located adjacent the heating chamber and, divided into a plurality of compartments by shelves for receiving microtiter plates, each compartment including a gate for closing the compartment off from the outside environment;
   a plurality of heaters, each heater being associated with one of said compartments; and
   gripping and transporting means having at least a portion extending between the heating chamber and incubation chamber, having a vertically displaceable working platform and a horizontally displaceable gripping arm, the gripping and transporting means for moving a microtiter plate between the heating chamber and selected compartment of the incubation chamber.

2. An incubation device as set forth in claim 1, wherein the heating chamber and the incubation chamber form a module in which the plurality of gates are arranged one above the other and are moveable along lateral guides.

3. An incubation device as set forth in claim 2, wherein the module includes means for individually opening the gates, the opening means including a plurality of catches, each catch being connected to a gate, and a vertically and horizontally movable gripping arm for engaging the catches.

4. An incubation device as set forth in claim 2, wherein the module further includes a storage hopper and a feed device for the microtiter plates.

5. An incubation device as set forth in claim 1, wherein the heating chamber and the incubation chamber form a module in which the gates are arranged one above another and are movable along lateral guides, the module being provided with a storage hopper, a feed device for the microtiter plates, and means for individually opening and closing the gates, and wherein the gripping and transporting means has a vertical axis and is rotatable about the vertical axis.

6. An incubation apparatus as set forth in claim 1, wherein the heaters are located an side walls of the compartments.

7. An incubation apparatus for microtiter plates, the apparatus comprising:
   a heating chamber for holding a microtiter plate and including a controllable hot air generator, means for closing the heating chamber off from the outside environment, air guide means for equalizing and distributing a stream of hot air to a microtiter plate, and air return means for collecting and returning air from the microtiter plate to the hot air generator;
   an incubation chamber, located adjacent the heating chamber and, divided into a plurality of compartments by shelves for receiving microtiter plates, each compartment including means for closing the compartment off from the outside environment;
   gripping and transporting means having at least a portion extending between the heating chamber and incubation chamber, for moving a microtiter plate between the heating chamber and a selected compartment of the incubation chamber; and
   means for selectively opening and closing the heating chamber and the incubation chamber to expose the heating chamber and the incubation chamber to the outside environment.

8. An incubation apparatus as set forth in claim 7, further including a plurality of heaters, each heater being disposed within a compartment of the incubation chamber.

9. An incubation apparatus as set forth in claim 7, wherein the compartments of the incubation chamber are vertically arranged in relation to the heating chamber.

10. An incubation apparatus as set forth in claim 9, wherein the compartments are arranged above the heating chamber.

11. An incubation apparatus as set forth in claim 9, wherein the gripping and transporting means include a vertically displaceable working platform and a horizontally displaceable gripping arm.

12. An incubation apparatus as set forth in claim 7, wherein the opening and closing means is connected to the gripping and transporting means.

* * * * *

UNITED STATES PATENT AND TRADEMARK OFFICE
CERTIFICATE OF CORRECTION

PATENT NO. : 5,149,654
DATED : September 22, 1992
INVENTOR(S) : Jurgen Gross et al It is certified that error appears in the above-identified patent and that said Letters Patent is hereby corrected as shown below:

Title page,
item [73] Assignee, change "Hoechst Aktiengesellschaft" to --Behringwerke Aktiengesellschaft--.

Abstract, line 2, before "heating" change "an" to --a-- and before "incubation" change "a" to --an--.

Claim 1, column 3, line 21, change "form" to --from--.

Claim 6, column 4, line 9, change "an" to --on--.

Claim 7, column 4, line 19, before, "air" (first occurrence) insert --hot--.

Claim 7, column 4, line 34, after "environment" insert--, the means for selectively opening and closing including portions

UNITED STATES PATENT AND TRADEMARK OFFICE
CERTIFICATE OF CORRECTION

PATENT NO. : 5,149,654
DATED : September 22, 1992
INVENTOR(S) : Jurgen Gross, et. al.

It is certified that error appears in the above-indentified patent and that said Letters Patent is hereby corrected as shown below:

located on the heating chamber and incubation chamber--.

Signed and Sealed this

Ninth Day of November, 1993

Attest:

Attesting Officer

BRUCE LEHMAN

Commissioner of Patents and Trademarks